United States Patent [19]

Tone et al.

[11] Patent Number: 4,684,648
[45] Date of Patent: Aug. 4, 1987

[54] ANTIMICROBIAL 1-SUBSTITUTED PHENYL-4-OXOQUINOLINE-3-CARBOXYLIC ACID COMPOUNDS AND COMPOSITIONS THEREOF

[75] Inventors: Hitoshi Tone; Hisashi Miyamoto; Hiraki Ueda; Kazuyuki Nakagawa, all of Tokushima, Japan

[73] Assignee: Otsuka Pharmaceutical Company Limited, Tokyo, Japan

[21] Appl. No.: 770,080

[22] Filed: Aug. 28, 1985

[30] Foreign Application Priority Data

May 10, 1985 [JP] Japan .................................. 60-100056
Jul. 22, 1985 [JP] Japan .................................. 60-162569

[51] Int. Cl.⁴ ..................... A61K 31/40; A61K 31/47; C07D 401/14
[52] U.S. Cl. .................................. 514/249; 514/254; 544/349; 544/363; 546/156
[58] Field of Search ................ 544/363, 349; 514/249, 514/254

[56] References Cited

U.S. PATENT DOCUMENTS 4,398,029 8/1983 Irikura et al. ...................... 544/363
4,571,396 2/1986 Hutt ................................... 514/249

FOREIGN PATENT DOCUMENTS 0131839 1/1985 European Pat. Off. .
2391210 12/1978 France .
2424919 11/1979 France .
2437406 4/1980 France .
0204193 11/1984 Japan ................................. 514/249
0204194 11/1984 Japan ................................. 514/249

1147336 4/1969 United Kingdom .

Primary Examiner—Sam Rosen
Assistant Examiner—Robert Benson
Attorney, Agent, or Firm—Wegner & Bretschneider

[57] ABSTRACT

Novel 1-substituted phenyl-4-oxoquinoline-3-carboxylic acid compounds of the formula:

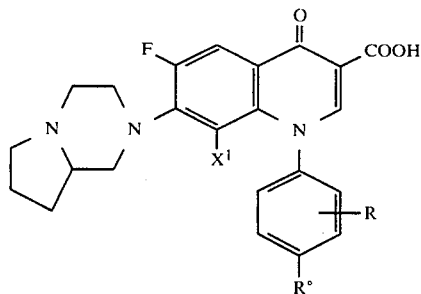

wherein R is hydrogen atom or fluorine atom, R° is hydroxy, fluorine atom or an alkanoyloxy having 1 to 6 carbon atoms, and $X^1$ is hydrogen atom or fluorine atom, and a pharmaceutically acceptable salt thereof, said compounds having excellent antimicrobial activity and hence being useful as an antimicrobial agent, and a pharmaceutical composition comprising as an active ingredient said 1-substituted phenyl-4-oxoquinoline-3-carboxylic acid compounds or a pharmaceutically acceptable salt thereof in admixture with a pharmaceutically acceptable diluent or carrier.

2 Claims, No Drawings

ANTIMICROBIAL 1-SUBSTITUTED PHENYL-4-OXOQUINOLINE-3-CARBOXYLIC ACID COMPOUNDS AND COMPOSITIONS THEREOF

The present invention relates to novel antimicrobial benzoheterocyclic compounds and salts thereof, more particularly 1-substituted phenyl-4-oxoquinoline-3-carboxylic acid compounds of the formula:

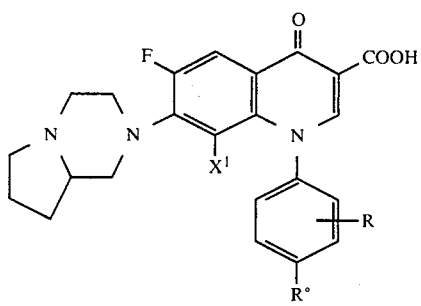

wherein R is a hydrogen atom or fluorine atom, $R^o$ is hydroxy, a fluorine atom or an alkanoyloxy having 1 to 6 carbon atoms, $X^1$ is a hydrogen atom or fluorine atom, and pharmaceutically acceptable salts thereof.

The benzoheterocyclic compounds of the formula [1] and salts thereof have excellent antibacterial activities against various gram positive and gram negative bacteria, and are useful for the treatment of various infectious diseases induced by various bacteria in human, other animals and fish and are also useful as an external antimicrobial or disinfectant agent for medical instruments or the like.

PRIOR ART

The following compounds have been published in Interscience Conference Antimicrobial Agents and Chemotherapy held on Oct. 8–10, 1984 (cf. Abstracts of The 984 ICAAC, page 102, Item 72).

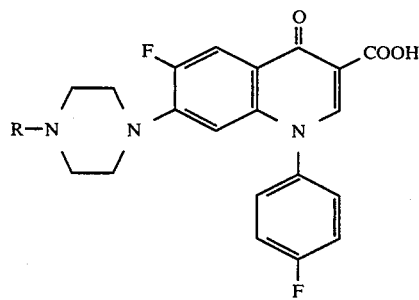

wherein R is hydrogen or methyl.

European Patent Publication No. 0131839 discloses the following compounds:

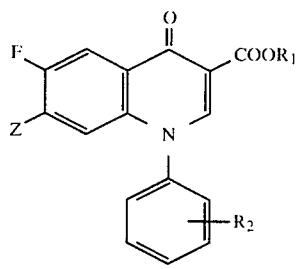

wherein $R_1$ is hydrogen or a carboxy protecting group, $R_2$ is hydrogen, halogen, nitro, carboxyl, cyano, methylenedioxy, an alkyl, a group of the formula: $-Y-R_3$ (Y is O or S, $R_3$ is hydrogen or an alkyl), an amine, and Z is an aliphatic monoheterocyclic ring including piperazine.

These known compounds are distinguished from the compounds [1] of the present invention in that no 1,4-diazabicyclo[4.3.0]nonan-1-yl group is included as the substituent (Z) at the 7-position of the benzoheterocyclic nucleus. The compounds of the present invention show superior antimicrobial activity to the above known compounds as is clear from comparative experiments disclosed hereinafter.

BRIEF DESCRIPTION OF THE INVENTION

The object of the present invention is to provide novel benzoheterocyclic compounds of the formula [1] and salts thereof which have excellent antimicrobial activity and excellent absorbability. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the formula [1], the term "alkanoyloxy having 1 to 6 carbon atoms" for $R^o$ includes straight chain or branched chain $C_1$-$C_6$ alkanoyloxy groups, such as formyloxy, acetyloxy, propionyloxy, butyryloxy, isobutyryloxy, pentanoyloxy, hexanoyloxy, etc., preferably an alkanoyloxy having 2 to 4 carbon atoms such as acetyloxy, propionyloxy, butyryloxy and isobutyryloxy, more preferably acetyloxy.

The group R is preferably substituted at the 2-position on the phenyl ring.

The group R is preferably a hydrogen atom, the group $R^o$ is preferably a hydroxy or an alkanoyloxy group having 1 to 6 carbon atoms, and the group $X^1$ is preferably hydrogen atom.

The compounds [1] and their salts of the present invention can be prepared by various processes, for example, by the process as shown in the following reaction schemes-I and -II.

[Reaction scheme-1]

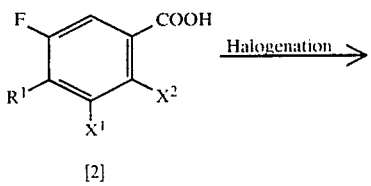

[2]

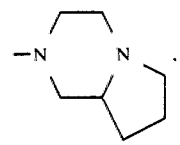

[3]

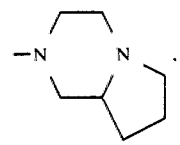

[5]

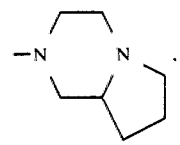

[7]

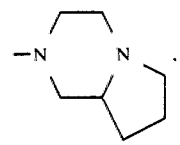

[9]

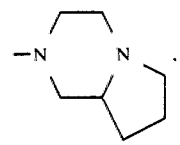

[10]

-continued
[Reaction scheme-1]

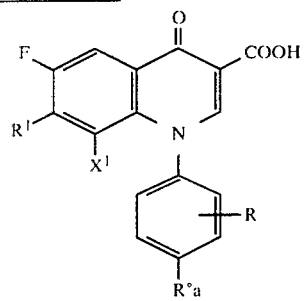

[11]

wherein $X^1$ is as defined above, $R^1$ is a halogen atom or a group of the formula:

$R^3$ is a group of the formula: $-COR^8$ (wherein $R^8$ is an alkyl having 1 to 6 carbon atoms) or a group of the formula: $-COOR^9$ (wherein $R^9$ is an alkyl having 1 to 6 carbon atoms), $R^4$ is an alkyl having 1 to 6 carbon atoms, $R^5$ is a group of the formula:

$$-N\begin{matrix}R^{10}\\R^{11}\end{matrix}$$

(wherein $R^{10}$ and $R^{11}$ are each an alkyl having 1 to 6 carbon atoms) or an alkoxy having 1 to 6 carbon atoms, $X^2$ and $X^3$ are each a halogen atom, $R^6$ and $R^7$ are each an alkyl having 1 to 6 carbon atoms, and $R^o$ is hydroxy, fluorine atom, or an alkoxy having 1 to 6 carbon atoms.

The halogenation of the compound [2] is carried out by reacting with a halogenating agent in the presence or absence of a solvent. The solvent includes aromatic hydrocarbons (e.g. benzene, toluene, xylene, etc.), halogenated hydrocarbons (e.g. dichloromethane, chloroform, carbon tetrachloride, etc.), ethers (e.g. dioxane, tetrahydrofuran, diethyl ether, etc.), dimethylformamide (DMF), dimethylsulfoxide (DMSO), and the like. The halogenating agent may be any conventional halogenating agents which can convert hydroxy in a carboxy group into a halogen atom, and includes, for example, thionyl chloride, phosphorus oxychloride, phosphorus oxybromide, phosphorus pentachloride, phosphorus pentabromide, and the like. The amounts of the compound [2] and the halogenating agent are not specified, but, in case of using no solvent, the halogenating agent is usually used in a large excess amount, and in case of using a solvent, the halogenating agent is usually used in an amount of at least 1 mole, preferably 2 to 4 moles, per 1 mole of the compound [2]. The reaction temperature and the reaction period of time are not specified, either, but the reaction is usually carried out at a temperature of from room temperature to 100° C. for 30 minutes to 6 hours.

The reaction of the compound [3] and the compound [4] is carried out in a suitable solvent in the presence of a basic compound. The solvent may be any conventional solvents unless they give any undesirable effect on the reaction, and includes, for example, water, ethers (e.g. diethyl ether, dioxane, tetrahydrofuran, monoglyme, diglyme, etc.), alcohols (e.g. methanol, ethanol, isopropanol, etc.), aromatic hydrocarbons (e.g. benzene, toluene, xylene, etc.), aliphatic hydrocarbons (e.g. n-hexane, heptane, cyclohexane, ligroin, etc.), amines (e.g. pyridine, N,N-dimethylaniline, etc.), halogenated hydrocarbons (e.g. chloroform, dichloromethane, carbon tetrachloride, etc.), aprotic polar solvents (e.g. DMF, DMSO, hexamethyl phosphoric triamide (HMPA), etc.), and a mixture of these solvents. The basic compound includes inorganic bases (e.g. metallic sodium, metallic potassium, metallic magnesium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, etc.), and organic bases (e.g. pyridine, piperidine, quinoline, triethylamine, N,N-dimethylaniline, etc.). The reaction is usually carried out at a temperature of from 0° to 150° C., preferably from room temperature to 120° C., for 0.5 to 15 hours. The compound [4] is usually used in an amount of at least 1 mole, preferably 1 to 2 moles, per 1 mole of the compound [3]. The basic compound is usually used in an amount of at least 1 mole, preferably 1 to 2 moles, per 1 mole of the compound [3].

The compound [5] wherein $R^3$ is the group: —$COR^8$ is subjected to the reaction for removal of the group: —$COR^8$ in a solvent in the presence of a basic compound. The solvent includes ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), aprotic polar solvents (e.g. DMF, DMSO, HMPA, etc.), and the like. The basic compound includes ammonia gas, aqueous ammonia, ammonium salts (e.g. ammonium chloride, etc.), primary or secondary amines (e.g. ethylamine, diethylamine, piperidine, etc.), and the like. The reaction is usually carried out at a temperature of from 0° to 150° C., preferably from room temperature to 100° C., for 1 to 20 hours.

The compound [5] wherein $R^3$ is a group: —$COOR^9$ is subjected to the reaction for removal of the group: —$COOR^9$ in an aqueous solution in the presence of an acid catalyst. The acid catalyst includes mineral acids (e.g. hydrochloric acid, sulfuric acid, etc.) and organic acids (e.g. p-toluenesulfonic acid, etc.). The reaction is usually carried out at a temperature of from 0° to 150° C., preferably from room temperature to 100° C., for 1 to 20 hours.

The reaction of the $R^3$ group-removed compound and the compound [6] is carried out in a suitable solvent. The solvent may be any solvents which are used in the above reaction for the removal of the $R^3$ group. The reaction is usually carried out at a temperature of from 0° to 150° C., preferably from 0° to 100° C., for 0.5 to 10 hours. The compound [6] is usually used in an equimolar to large excess amount, preferably 1 to 2 moles per 1 mole of the compound [5]. In case of using a compound [6] wherein $R^5$ is a lower alkoxy group, the reaction may also be carried out by using acid anhydrides (e.g. acetic anhydride) as a solvent as well as above-mentioned solvents at a temperature of from 0° to 200° C., preferably 0° to 170° C.

The reaction of the compound [7] and the compound [8] is carried out in a suitable solvent. The solvent may be any conventional solvents unless they give any undesirable effect on the reaction, and includes, for example, alcohols (e.g. methanol, ethanol, propanol), ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The reaction is usually carried out at a temperature of from 0° to 150° C., preferably from room temperature to 100° C., for 0.5 to 15 hours. The compound [8] is usually used in an amount of at least 1 mole, preferably 1 to 2 moles, per 1 mole of the compound [7].

The cyclization of the compound [9] is carried out in a suitable solvent in the presence of a basic compound. The solvent may be any conventional solvents unless they give any undesirable effect on the reaction, and includes, for example, ethers (e.g. diethyl ether, dioxane, tetrahydrofuran, monoglyme, diglyme, etc.), aliphatic hydrocarbons (e.g. n-hexane, heptane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The basic compound includes inorganic bases (e.g. metallic sodium, metallic potassium, sodium hydride, sodium amide, sodium hydroxide, potassium hydroxide, etc.), metal alcoholates (e.g. sodium methylate, sodium ethyate, etc.), and organic bases (e.g. 1,8-diazobicyclo[5.4.0]undecene-7 (DBU), N-benzyltrimethylammonium hydroxide, tetrabutylammonium hydroxide, etc.). The reaction is usually carried out at a temperature of from 0° to 150° C., preferably from room temperature to 120° C., for 0.5 to 5 hours. The basic compound is usually used in an amount of at least 1 mole, preferably 1 to 2 moles, per 1 mole of the compound [9].

The hydrolysis of the compound [10] can be carried out under the conditions of conventional hydrolysis, for instance, in the presence of a basic compound (e.g. sodium hydroxide, potassium hydroxide, barium hydroxide, etc.), a mineral acid (e.g. sulfuric acid, hydrochloric acid, nitric acid, hydrobromic acid, etc.) or an organic acid (e.g. acetic acid, aromatic sulfonic acids, etc.) in a solvent such as water, alcohols (e.g. methanol, ethanol, isopropanol, etc.), ketones (e.g. acetone, methyl ethyl ketone, etc.), ethers (e.g. dioxane, ethylene glycol, etc.), acetic acid, or a mixture thereof. The reaction is usually carried out at a temperature of from room temperature to 200° C. preferably 50° to 150° C., for 0.5 to 6 hours. By the reaction, there is produced the compound [11].

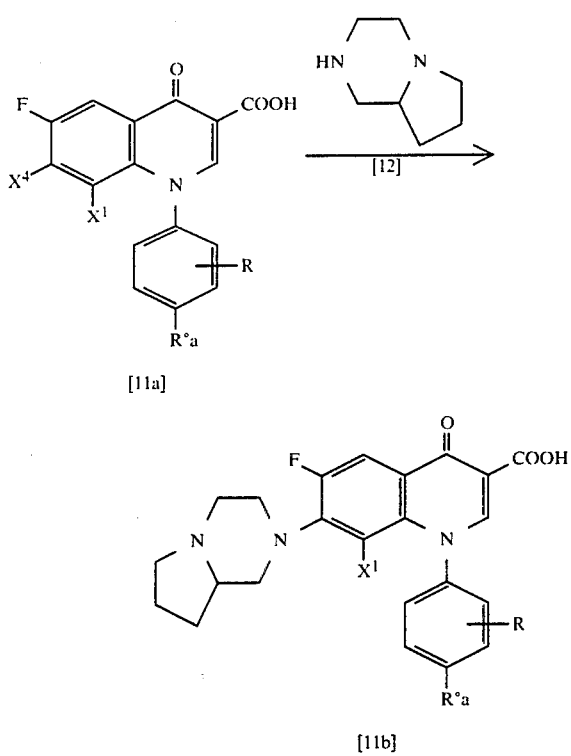

wherein R, R°a and X¹ are as defined above, and X⁴ is a halogen atom.

The reaction of the compound [11a] and the compound [12] is carried out in a solvent, wherein both compounds are used in a wide range of ratio, and the compound [12] is usually used in an amount of at least 1 mole, preferably 1 to 5 moles, per 1 mole of the compound [11a]. The solvent includes water, alcohols (e.g. methanol, ethanol, isopropanol, butanol, amyl alcohol, isoamyl alcohol, etc.), aromatic hydrocarbons (e.g. benzene, toluene, xylene, etc.), ethers (e.g. tetrahydrofuran, dioxane, diglyme, etc.), DMF, DMSO, HMPA, N-methylpyrrolidone, or the like. Among these solvents, the preferred one is DMF, DMSO, HMPA, and N-methylpyrrolidone. The reaction may also be carried out in the presence of an acid-removing agent, such as inorganic carbonates (e.g. sodium carbonate, potassium carbonate, sodium hydrogen carbonate, potassium hydrogen carbonate, etc.) or tertiary amines (e.g. pyridine, quinoline, triethylamine, etc.). The reaction is usually carried out under a pressure of from 1 to 20 atm., preferably from 1 to 10 atm., at a temperature of from 100° to 250° C., preferably 100° to 200° C., for 0.5 to 20 hours.

The compound [1] wherein R° is hydroxy can be converted into the corresponding compound wherein R° is an alkanoyloxy having 1 to 6 carbon atoms by treating it with an alkanoylation agent. The alkanoylation agent includes a compound of the formula: $(R^{12})_2O$ or $R^{12}X^5$ wherein $R^{12}$ is an alkanoyl having 1 to 6 carbon atoms and $X^5$ is a halogen atom. The reaction can be carried out in the presence or absence of a solvent. The solvent may be any conventional solvents unless they give any undesirable effect on the reaction, and includes, for example, halogenated hydrocarbons (e.g. dichloromethane, dichloroethane, chloroform, carbon tetrachloride), aromatic hydrocarbons (e.g. benzene, toluene, xylene), ethers (e.g. diethyl ether, tetrahydrofuran, dioxane), pyridine, and the like. The alkanoylation agent is used in an amount of at least equimolar to the starting compound, preferably in an excess amount. The reaction is usually carried out at a temperature of from 0° to 150° C., preferably from 0° to 100° C., for 1 to 24 hours. The above reaction may also be carried out in the presence of a tertiary amine (e.g. pyridine, triethylamine).

The compound [11] or [11b] wherein R°a is an alkoxy having 1 to 6 carbon atoms can be converted into the corresponding compound wherein R°a is hydroxy by treating it with an acid in a solvent or without using any solvent. The solvent includes water, aromatic hydrocarbons (e.g. nitrobenzene, toluene, benzene, etc.), saturated hydrocarbons (e.g. hexane, octane, etc.), lower alcohols (e.g. methanol, ethanol, isopropanol, etc.), ethers (dioxane, tetrahydrofuran, etc.), ketones (e.g. acetone, etc.), acetic acid, acetonitrile, and a mixture thereof. The acid includes mineral acids (e.g. hydrobromic acid, etc.), aluminum chloride, tin chloride, boron fluoride, zinc chloride, boron tribromide, boron trichloride, and the like. These acids may be used in an amount at least equimolar to the starting compound, and usually in a large excess amount. The reaction is usually carried out at a temperature of from $-30°$ to 200° C., preferably from $-30°$ to 150° C., for 0.5 to 8 hours.

The compound [10] in Reaction Scheme-I wherein R°a is an alkoxy having 1 to 6 carbon atoms can be converted into the corresponding compound wherein R°a is hydroxy in the same manner as described above.

The compounds [1] can easily be converted into a salt thereof by treating them with a pharmaceutically acceptable acid or base. The acid includes inorganic acids (e.g. hydrochloric acid, sulfuric acid, phosphoric acid, hydrobromic acid, etc.) and organic acids (e.g. succinic acid, maleic acid, fumaric acid, malic acid, tartaric acid, citric acid, benzoic acid, etc.). The base includes sodium hydroxide, potassium hydroxide, calcium hydroxide, sodium carboante, potasium hydrogen carbonate, and the like.

The compound thus obtained can easily be isolated by conventional methods, such as extraction with solvents, dilution method, recrystallization, column chromatography, preparative thin layer chromatography, and the like.

The compounds [1] of the present invention show particularly excellent antimicrobial activity against *Staphylococcus aureus, Staphylococcus pyrogenes,* Pseudomonas, anaerobe, various resistant strains of gram positive or negative bacteria, and hence, are useful as an antimicrobial agent for the treatment of diseases induced by these microorganisms. These compounds show also low toxicity and less side effect and are characteristic in good absorbability and in sustained activity. Moreover, the compounds are highly excreted via urine and hence are useful for the treatment of urinary infectious diseases, and further because of easy excretion via bile, they are also useful for the treatment of intestinal infectious diseases.

The compounds of the present invention are usually used in the form of a usual pharmaceutical preparation. The pharmaceutical preparation can be prepared in admixture with conventional pharmaceutically acceptable diluents or carriers, such as fillers, weighting agents, binding agents, wetting agents, disintegrators, surfactants, lubricating agents, and the like. The pharmaceutical preparation includes various preparations suitable for treatment of the diseases, for example, tablets, pills, powders, solutions, suspensions, emulsions, granules, capsules, suppositories, injections (solutions, suspensions, etc.), and the like. In the preparation of tablets, there may be used any conventional carriers, for example, vehicles (e.g. lactose, white sugar, sodium chloride, glucose, urea, starches, calcium carbonate, kaolin, crystalline cellulose, silicate, etc.), binding agents (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carriers, such as vehicles (e.g. glucose, lactose, starches, cacao butter, hydrogenated vegetable oils, kaolin, talc, etc.), binding agents (e.g. gum arabic powder, tragacanth powder, gelatin, ethanol, etc.), disintegrators (e.g. laminaran, agar, etc.), and the like. In the preparation of suppositories, there may be used conventional carriers, such as polyethylene glycol, cacao butter, higher alcohols, higher alcohol esters, gelatin, semi-synthetized glycerides, and the like. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, ethyl alcohol, propylene glycol, ethoxylated isostearyl alcohol, polyoxylated isostearyl alcohol, polyoxyethylene sorbitan fatty acid esters, and the like. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweeting agents, and other medicaments. The preparations in the form of a paste, cream or gel may be prepared by using as a diluent white vaseline, paraffin, glycerin, cellulose derivatives, polyethylene glycol, silicone, bentonite, or the like.

The active compounds [1] or salts thereof may be contained in any amount in the preparations, and are usually contained in an amount of 1 to 70% by weight based on the whole weight of the preparations.

The pharmaceutical preparations of the present invention can be administered in any methods. Suitable methods for administration may be selected in accordance with the preparation form, age and sex of the patients, degree of severity of the diseases, and the like. For instance, tablets, pills, solutions, suspensions, emulsions, granules and capsules are administered in oral route. In case of injection, it is administered intravenously alone or together with an auxiliary liquid (e.g. glucose, amino acid solution). The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of the patients, severity of the diseases, and the like, but is usually in the range of about 0.2 to 100 mg of the active compound [1] or a salt thereof per 1 kg of body weight of the patient per day. The preparation is usually administered by dividing into 2 to 4 times per day.

The present invention is illustrated by the following Reference Examples, Examples, Preparations, and Experiments.

REFERENCE EXAMPLE 1

Thionyl chloride (70 ml) is added to 2-bromo-4,5-difluorobenzoic acid (39.5 g), and the mixture is allowed to stand at room temperature for one hour and then refluxed for one hour. After completion of the reaction, the excess thionyl chloride is distilled off under reduced pressure. The oily residue is distilled under reduced pressure to give 2-bromo-4,5-difluorobenzoyl chloride (37.8 g) as a pale yellow oily substance, b.p. 121°–123° C. (32 mmHg).

REFERENCE EXAMPLE 2

To a mixture of ethyl acetacetate (13.0 g), ligroin (16 ml) and water (32 ml) is added 33% aqueous sodium hydroxide (4.4 ml) with stirring under ice-cooling. To the mixture are gradually added a solution of 2-bromo-4,5-difluorobenzoyl chloride (25.6 g) in ligroin (14 ml) and 33% aqueous sodium hydroxide (18 ml) with stirring under ice-cooling. After the addition, the mixture is stirred at room temperature for 14 hours. The precipitated crystals are separated by filtration and washed with water. The fitrate is weakly acidified with ammonium chloride and extracted with dichloromethane. The crystals collected above are dissolved in methanol (200 ml) and thereto is added ammonium chloride (20 g). The mixture is stirred at room temperature for one hour and then extracted with dichloromethane. This extract is combined with the dichloromethane extract obtained above, dired over sodium sulfate, and then the solvent is distilled off to give ethyl 2-acetyl-2-(2-bromo-4,5-difluorobenzoyl)acetate (30.1 g) as a yellow oily substance.

NMR (CDCL$_3$) δ: 17.20 (bs, 1H), 7.38 (dd, 1H, J=9 Hz, 7 Hz), 7.10 (dd, 1H, J=9.5 Hz, 8.5 Hz), 3.97 (q, 2H, J=6 Hz), 2.53 (s, 3H), 1.93 (t, 3H, J=6 Hz)

REFERENCE EXAMPLE 3

Ethyl 2-acetyl-2-(2-bromo-4,5-difluorobenzoyl)acetate (24.3 g) is dissolved in anhydrous diethyl ether (50 ml), and thereto is slowly passed ammonia gas under ice-cooling for 45 minutes. The mixture is allowed to stand at room temperature for 17 hours. To the reaction mixture are added dichloromethane and water, and the mixture is acidified with 1N hydrochloric acid and the dichloromethane layer is separated. The dichloromethane layer is washed with saturated aqeuous sodium chloride, dried over sodium sulfate, and the solvent is distilled off. To the residue are added anhydrous benzene (65 ml) and DMF-dimethylacetal (11 ml), and the mixture is refluxed for 2 hours. The solvent is distilled off, and the resulting residue is purified by silica gel column chromatography (solvent, dichloromethane:methanol = 80:1) to give ethyl 2-(2-bromo-4,5-difluorobenzoyl)-3-dimethylaminoacrylate (9.0 g) as an orange color oily substance.

NMR (CDCL$_3$) δ: 7.83 (s, 1H), 7.33 (dd, 1H, J=9 Hz, 8.5 Hz), 7.19 (dd, 1H, J=11 Hz, 8.5 Hz), 3.94 (q, 2H, J=7 Hz), 3.30 (bs, 3H), 3.02 (bs, 3H), 1.95 (t, 3H, J=7 Hz)

REFERENCE EXAMPLE 4

Ethyl 2-(2-bromo-4,5-difluorobenzoyl)-3-dimethylaminoacrylate (2.18 g) and p-anisidine (0.9 g) are dissolved in anhydrous benzene (12 ml), and the mixture is stirred at room temperature for 2 hours. After completion of the reaction, the benzene layer is taken out, washed with diluted hydrochloric acid and saturated aqueous sodium chloride in order, and dried over sodium sulfate. The solvent is distilled off, and the resulting residue is purified by silica gel column chromatography (solvent, dichloromethane) to give ethyl 2-(2-bromo-4,5-difluorobenzoyl)- 3-p-anisidylacrylate (2.09 g) in the form of a mixture of trans and cis isomers (3:1) as a yellow sold, m.p. 98°–104° C.

REFERENCE EXAMPLE 5

The cis-trans mixture of ethyl 2-(2-bromo-4,5-difluorobenzoyl)-3-p-anisidylacrylate (2.04 g) obtained in Reference Example 4 is dissolved in anhydrous dioxane (40 ml), and thereto is added 60% sodium hydride (0.24 g), and the mixture is stirred at room temperature for one hour and further refluxed for one hour. After allowing to cool, the reaction mixture is poured into saturated aqueous ammonium chloride under ice-cooling. The precipitated crystals are separated by filtration, washed with water, and then purified by silica gel column chromatography (solvent, dichloromethane:methanol = 80:1). The product is recrystallized from ethanol to give ethyl 6,7-difluoro-1-(4-methoxyphenyl)-1,4-dihydro-4-oxoquinoline-3-carboxylate (1.40 g) as colorless needles, m.p. 212°–214° C.

REFERENCE EXAMPLE 6

Magnesium ribbon (7.3 g) is suspended in absolute ethanol (15 ml), and thereto is added carbon tetrachloride (1.5 ml), and thereto is added dropwise a mixture of diethyl malonate (48 g), absolute ethanol (30 ml) and anhydrous ether (120 ml) over a period of one hour. After the addition, the mixture is refluxed for 2 hours. After cooling till room temperature, a solution of 2-bromo-4,5-difluorobenzoyl chloride (92 g) in anhydrous ether (50 ml) is added dropwise to the mixture. After the addition, the mixture is allowed to stand overnight at room temperature. A mixture of ice-water (120 ml) and conc. sulfuric acid (8 ml) is added dropwise to the reaction mixture under ice-cooling. After the addition, the mixture is extracted with ether. The ether layer is washed with saturated aqueous sodium chloride solution and dried over magnesium sulfate. The solvent is distilled off under reduced pressure to give diethyl (2-bromo-4,5-difluorobenzoyl)malonate (123 g).

REFERENCE EXAMPLE 7

To a solution of diethyl (2-bromo-4,5-difluorobenzoyl)malonate (75.6 g) in water (100 ml) is added p-toluenesulfonic acid (0.3 g), and the mixture is refluxed for 3 hours. After cooling, the reaction mixture is extracted with dichloromethane. The dichloromethane layer is washed with saturated aqueous sodium chloride solution and dried over magnesium sulfate. After distilling off the solvent under reduced pressure, the residue is distilled to give ethyl (2-bromo-4,5-difluorobenzoyl)acetate (52.0 g), b.p. 105°–115° C. (0.15 mmHg).

REFERENCE EXAMPLE 8

A mixture of ethyl (2-bromo-4,5-difluorobenzoyl)acetate (52.0 g), ethyl orthoformate (36.6 g) and acetic anhydride (41.6 g) is heated at 150° C. for 2 hours. After the reaction, the reaction mixture is concentrated under reduced pressure. The resulting residue is purified by silica gel column chromatography (solvent, dichloromethane:n-hexane = 2:1) to give ethyl 2-(2-bromo-4,5-difluorobenzoyl)-3-ethoxyacrylate (49 g).

REFERENCE EXAMPLE 9

Ethyl 2-(2-bromo-4,5-difluorobenzoyl)-3-dimethylaminoacrylate (1.09 g) and 2-fluoro-4-methoxyaniline (0.51 g) are dissolved in benzene (10 ml), and the mixture is allowed to stand at room temperature for 2 hours. The reaction mixture is washed with diluted hydrochloric acid and saturated aqueous sodium chloride, and dried over sodium sulfate. After distilling off the solvent, the residue is dissolved in anhydrous dioxane (20 ml) and thereto is added 60% sodium hydride (0.14 g). The mixture is stirred at room temperature for one hour and further refluxed for one hour. After cooling, the reaction mixture is poured into saturated aqueous ammonium chloride under ice-cooling. The precipitated crystals are separated by filtration, washed with water, purified by silica gel column chromatography (solvent, dichloromethane:methanol = 80:1), and then recrystallized from ethanol to give ethyl 6,7-difluoro-1-(2-fluoro-4-methoxyphenyl)-1,4-dihydro-4-oxoquinoline-3-carboxylate (0.59 g) as pale yellow needles, m.p. 170°–171° C.

REFERENCE EXAMPLE 10

To ethyl 6,7-difluoro-1-(4 -methoxyphenyl)-1,4-dihydro-4-oxoquinoline-3-carboxylate (0.61 g) are added 90% acetic acid (8.0 ml) and conc. hydrochloric acid (2.0 ml), and the mixture is heated with stirring at 110° C. for 2 hours. After the reaction, the solvent is distilled off under reduced pressure. The resulting residue is washed well with water to give 6,7-difluoro-1-(4-methoxyphenyl)-1,4-dihydro-4-oxoquinoline-3-carboxylic acid (0.54 g) as colorless needles, m.p. 256°–258° C.

REFERENCE EXAMPLE 11

In the same manner as described in Reference Example 10 using an appropriate starting material, the following compound is prepared.

6,7-Difluoro-1-(4-fluorophenyl)-1,4-dihydro-4-oxoquinoline-3-carboxylic acid, colorless needles, m.p. 263°–265° C.

REFERENCE EXAMPLE 12

To ethyl 6,7-difluoro-1-(4-methoxyphenyl)-1,4-dihydro-4-oxoquinoline-3-carboxylate (0.70 g) is added 48% hydrobromic acid (8 ml), and the mixture is stirred at 100°–110° C. for 3 hour. After cooling, the precipitated crystals are separated by filtration, washed with water and recrystallized from dichloromethane-ethanol to give 6,7-difluoro-1-(4-hydroxyphenyl)-1,4-dihydro-4-oxoquinoline-3-carboxylic acid (0.57 g) as colorless needles, m.p. 288°–290° C.

REFERENCE EXAMPLE 13

Magnesium ribbon (0.11 g) is suspended in absolute ethanol (0.5 ml), and thereto is added carbon tetrachloride (0.05 ml). After 10 minutes, to the mixture is added dropwise a mixture of diethyl malonate (1.5 ml), absolute ethanol (0.9 ml) and anhydrous ether (3.8 ml) at room temperature. After the addition, the mixture is refluxed for 3 hours. Thereafter, a solution of 2,3,4,5-tetrafluorobenzoyl chloride (2.0 g) in anhydrous ether (0.9 ml) is added dropwise to the mixture under ice-cooling. After the addition, the mixture is stirred at room temperature for 3 hours and allowed to stand overnight. A mixture of ice-water (4 ml) and conc. sulfuric acid (0.24 ml) is added dropwise to the reaction mixture under ice-cooling. After the addition, the mixture is stirred at room temperature for 30 minutes. The ether layer is separated, and the remaining solution is extracted with ether. The ether layers are combined and washed with saturated aqueous sodium chloride solution and dried over magnesium sulfate. The solvent is distilled off under reduced pressure to give diethyl (2,3,4,5-tetrafluorobenzoyl)malonate (3.0 g).

To water (5 ml) are added diethyl (2,3,4,5-tetrafluorobenzoyl)malonate (2.9 g) obtained above and p-toluenesulfonic acid (15 mg), and the mixture is refluxed for 3 hours. After cooling, the reaction mixture is extracted with dichloromethane. The dichloromethane layer is washed with saturated aqueous sodium chloride solution and dried over magnesium sulfate. After distilling off the solvent under reduced pressure, the residue is purified by silica gel column chromatography (solvent, chloroform:n-hexane=1:1) to give α-(2,3,4,5-tetrafluorobenzoyl)acetate (0.8 g), m.p. 44.5°–45.5° C.

REFERENCE EXAMPLE 14

A mixture of ethyl α-(2,3,4,5-tetrafluorobenzoyl)acetate (0.7 g), ethyl orthoformate (0.67 g) and acetic anhydride (0.74 g) is heated at 150° C. for 1.5 hours. After the reaction, the volatile material is distilled off at 120° C. under reduced pressure with a water pump to give ethyl 2-(2,3,4,5-tetrafluorobenzoyl)-3-ethoxyacrylate (0.8 g) in the form of a mixture of cis and trans isomers.

NMR (CDCl$_3$) δ: 7.70, 7.75 (s, 1H), 7.28–7.61 (m, 1H), 4.02–4.46 (m, 4H), 1.05–1.52 (m, 6H)

REFERENCE EXAMPLE 15

A mixture of ethyl 2-(2,3,4,5-tetrafluorobenzoyl)-3-ethoxyacrylate (0.4 g), p-anisidine (0.15 g) and ethanol (4 ml) is stirred at room temperature for 30 minutes. After the reaction, the solvent is distilled off under reduced pressure. To the resulting residue is added anhydrous dioxane (10 ml) and further added portionwise 60% sodium hydride (60 mg). The mixture is stirred at room temperature for 30 minutes. Thereafter, the reaction mixture is poured into saturated aqueous ammonium chloride and then extracted with dichloromethane to give ethyl 6,7,8-trifluoro-1-(4-methoxyphenyl)-1,4-dihydro-4-oxoquinoline-3-carboxylate (0.37 g).

REFERENCE EXAMPLE 16

A mixture of ethyl 6,7,8-trifluoro-1-(4-methoxyphenyl)-1,4-dihydro-4-oxoquinoline-3-carboxylate (0.37 g), conc. hydrochloric acid (1 ml) and 90% acetic acid (4 ml) is heated at 120° C. for one hour. After cooling, the precipitated crystals are separated by filtration, washed well with water and with a mixture of ethanol and ether to give 6,7,8-trifluoro-1-(4-methoxyphenyl)-1,4-dihydro-4-oxoquinoline-3-carboxylic acid (0.3 g) as white crystals, m.p. 252°–254° C.

REFERENCE EXAMPLES 17

A mixture of ethyl 6,7,8-trifluro-1-(4-methoxyphenyl)-1,4-dihydro-4-oxoquinoline-3-carboxylate (0.37 g) and 47% hydrobromic acid (4 ml) is heated at 120° C. for 3 hours. After cooling, the precipitated crystals are separated by filtration, washed with water and further with a mixture of ethanol and ether to give 6,7,8-trifluoro-1-(4-hydroxyphenyl)-1,4-dihydro-4-oxoquinoline-3-carboxylic acid (0.26 g), m.p. >300° C., white crystals.

NMR (trifluoroacetic acid) δ: 9.33 (s, 1H), 8.46 (dt, 1H, J=10 Hz, 7.5 Hz, 2.5 Hz), 7.56 (d, 2H, J=9 Hz), 7.27 (d, 2H, J=9 Hz).

EXAMPLE 1

6,7-Difluoro-1-(4-hydroxyphenyl)-1,4-dihydro-4-oxoquinoline-3-carboxylic acid (0.10 g) is suspended in N-methylpyrrolidone (2 ml), and thereto is added 1,4-diazabicyclo[4.3.0]nonane (0.19 g), and the mixture is stirred at 90° C. for 30 minutes. After completion of the reaction, the solvent is distilled off under reduced pressure, and the residue is washed with ethanol and recrystallized from DMF to give 6-fluoro-1-(4-hydroxyphenyl)-7-(1,4-diazabicyclo[4.3.0]nonan-1-yl)-1,4-dihydro-4-oxoquinoline-3-carboxylic acid (0.06 g) as colorless crystals, m.p. 296°–301° C. (decomp.)

Elementary analysis for $C_{23}H_{22}N_3O_4F$: Calcd. (%): C,65.24; H,5.24; N,9.92 Found (%): C,65.20; H,5.27, N,9.94.

EXAMPLES 2–4

In the same manner as described in Example 1 using appropriate starting materials, the compounds as shown in Table 1 are prepared.

TABLE 1

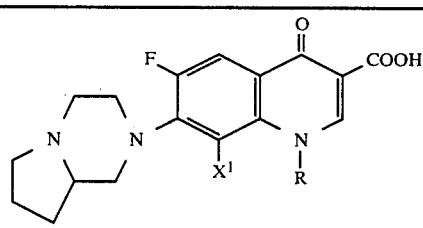

| Ex. No. | X$^1$ | R | M.p. (°C.) (Recrystalliz. solvent) | Crystalline form |
|---|---|---|---|---|
| 2 | F | —⟨⟩—OH | 298–302 (dec.) (Dimethylformamide) | Pale yellowish white crystals |
| 3 | H | —⟨⟩—OH (F) | 270–274 (dec.) (DMF-ethanol) | Pale yellowish white crystals |
| 4 | H | —⟨⟩—F | 262–265 (dec.) (Ethyl acetate) | Pale yellowish white crystals |

EXAMPLE 5

6-Fluoro-7-(1,4-diazabicyclo[4.3.0]nonan-1-yl)-1-(2-fluoro-4-hydroxyphenyl)-1,4-dihydro-4-oxoquinoline-3-carboxylic acid (0.14 g) is dissolved in dry pyridine (5 ml) and acetic anhydride (5 ml), and the mixture is allowed to stand at room temperature for 16 hours. Excess acetic anhydride and pyridine are distilled off under reduced pressure, and the residue is dissolved in dichloromethane. The dichloromethane solution is washed with diluted hydrochloric acid, saturated aqueous sodium chloride, saturated aqueous sodium hydrogen carbonate, and saturated aqueous sodium chloride in this order, and dried over sodium sulfate. The solvent is distilled off, and the resulting residue is recrystallized from ethanol to give 6-fluoro-7-(1,4-diazabicyclo[4.3.0-]nonan-1-yl)-1-(2-fluoro-4-acetyloxyphenyl)-1,4-dihydro-4-oxoquinoline-3-carboxylic acid (0.10 g) as pale yellowish white crystals, m.p. 206°–207° C.

Elementary analysis for $C_{25}H_{23}N_3O_4F_2$: Calcd. (%): C,62.10; H,4.79; N,8.69 Found (%): C,62.07; H,4.84, N,8.64.

EXAMPLE 6

6-Fluoro-7-(1,4-diazabicyclo[4.3.0]nonan-1-yl)-1-(4-hydroxyphenyl)-1,4-dihydro-4-oxoquinoline-3-carboxylic acid (0.14 g) is dissolved in dry pyridine (5 ml) and acetic anhydride (5 ml), and the mixture is allowed to stand at room temperature for 16 hours. Excess acetic anhydride and pyridine are distilled off under reduced pressure, and the residue is dissolved in dichloromethane. The dichloromethane solution is washed with diluted hydrochloric acid, saturated aqueous sodium chloride, saturated aqueous sodium hydrogen carbonate, and saturated aqueous sodium chloride in this order, and dried over sodium sulfate. The solvent is distilled off, and the resulting residue is recrystallized from ethanol to give 6-fluoro-7-(1,4-diazabicyclo[4.3.0]nonan-1-yl)-1-(4-acetyloxyphenyl)-1,4-dihydro-4-oxoquinoline-3-carboxylic acid (0.12 g) as pale yellowish white crystals, m.p. 224°–225.5° C. (dec.)

Elementary analysis for $C_{25}H_{24}N_3O_5F$: Calcd. (%): C,64.50; H,5.20; N,9.03 Found (%): C,64.52; H,5.24, N,8.99.

EXAMPLE 7

6,8-Difluoro-7-(1,4-diazabicyclo[4.3.0]nonan-1-yl)-1-(4-hydroxyphenyl)-1,4-dihydro-4-oxoquinoline-3-carboxylic acid (0.14 g) is dissolved in dry pyridine (5 ml) and acetic anhydride (5 ml), and the mixture is allowed to stand at room temperature for 16 hours. Excess acetic anhydride and pyridine are distilled off under reduced pressure, and the residue is dissolved in dichloromethane. The dichloromethane solution is washed with diluted hydrochloric acid, saturated aqueous sodium chloride, saturated aqueous sodium hydrogen carbonate, and saturated aqueous sodium chloride in this order, and dried over sodium sulfate. The solvent is distilled off, and the resulting residue is recrystallized from ethanol to give 6,8-difluoro-7-(1,4-diazabicyclo[4.3.0-]nonan-1-yl)-1-(4-acetyloxyphenyl)-1,4-dihydro-4-oxoquinoline-3-carboxylic acid (0.09 g) as pale yellowish white crystals, m.p. 230°–232° C.

Elementary analysis for $C_{25}H_{23}N_3O_5F_2$: Calcd. (%): C,62.10; H,4.79; N,8.69 Found (%): C,62.13; H,4.82, N,8.71.

PREPARATION 1

An injection preparation is prepared from the following components.

| Components | Amount |
|---|---|
| 6-Fluoro-1-(4-hydroxyphenyl)-7-(1,4-diaza- | 200 mg |
| bicyclo[4.3.0]nonan-1-yl)-1,4-dihydro-4-oxoquinoline-3-carboxylic acid | |
| Glucose | 250 mg |
| Distilled water for injection | q.s. |
| Totally | 5 ml |

6-Fluoro-1-(4-hydroxyphenyl)-7-(1,4-azabicyclo[4.3.0]nonan-1-yl)-1,4-dihydro-4-oxoquinoline-3-carboxylic acid and glucose are dissolved in distilled water for injection, and the solution is added to a 5 ml ampoule, which is purged with nitrogen gas and then subjected to sterilization at 121° C. for 15 minutes to give an injection preparation.

PREPARATION 2

Film coated tablets are prepared from the following components.

| Components | Amount |
|---|---|
| 6,8-Difluoro-1-(4-hydroxyphenyl)-7-(1,4-diazabicyclo[4.3.0]nonan-1-yl)-1,4-dihydro-4-oxoquinoline-3-carboxylic acid | 100 g |
| Avicel (tradename of microcrystalline cellulose, manufactured by Asahi Chemical, Japan) | 40 g |
| Corn starch | 30 g |
| Magnesium stearate | 2 g |
| TC-5 (tradename of hydroxypropyl methylcellulose, manufactured by Shinetsu Kagaku Kogyo, Japan) | 10 g |
| Polyethylene glycol 6000 | 3 g |
| Castor oil | 40 g |
| Ethanol | 40 g |

6,8-Difluoro-1-(4-hydroxyphenyl)-7-(1,4-diazabicyclo[4.3.0]nonan-1-yl)-1,4-dihydro-4-oxoquinoline-3-carboxylic acid, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

PREPARATION 3

An ointment is prepared from the following components.

| Components | Amount |
|---|---|
| 6-Flouro-1-(4-hydroxyphenyl)-7-(1,4-diazabicyclo[4.3.0]nonan-1-yl)-1,4-dihydro-4-oxoquiolione-3-carboxylic acid | 2 g |
| Purified lanolin | 5 g |
| Bleached beeswax | 5 g |
| White vaseline | 88 g |
| Totally | 100 g |

Bleached beeswax is made liquid by heating, and thereto are added 6-fluoro-1-(4-hydroxyphenyl)-7-(1,4-diazabicyclo[4.3.0]nonan-1-yl)-1,4-dihydro-4-oxoquinoline-3-carboxylic acid, purified lanolin and while vaseline, and the mixture is heated until it becomes liquid. The mixture is stirred until it is solidified to give an ointment.

EXPERIMENT 1

(Antimicrobial activity in in vitro)

The antimicrobial activity of the test compounds as mentioned below was tested by measuring minimum inhibitory concentration (MIC) by the serial dilution method on agar plate [cf. Chemotherapy, 22, 1126–1128 (1974)]. The microorganisms were used in a concentration of $1 \times 10^8$ cells/ml (O.D. 660 mµ, 0.07–0.16) and $1 \times 10^6$ cells/ml (100 folds dilution). The results are shown in Table 2. [Test compound]:

1. 6-Fluoro-1-(4-hydroxyphenyl)-7-(1,4-diazabicyclo[4.3.0]nonan-1-yl)-1,4-dihydro-4-oxoquinoline-3-carboxylic acid
2. 6,8-Difluoro-1-(4-hydroxyphenyl)-7-(1,4-diazabicyclo[4.3.0]nonan-1-yl]-1,4-dihydro-4-oxoquinoline-3-carboxylic acid
3. 6-Fluoro-1-(2-fluoro-4-hydroxyphenyl)-7-(1,4-diazabicyclo[4.3.0]nonan-1-yl)-1,4-dihydro-4-oxoquinoline-3-carboxylic acid
4. 6-Fluoro-1-(2-fluoro-4-acetyloxyphenyl)-7-(1,4-diazabicyclo[4.3.0]nonan-1-yl)-1,4-dihydro-4-oxoquinoline-3-carboxylic acid
5. 6-Fluoro-1-(4-acetyloxyphenyl)-7-(1,4-diazabicyclo[4.3.0]nonan-1-yl)-1,4-dihydro-4-oxoquinoline-3-carboxylic acid
A. 6-Fluoro-1-(4-fluorophenyl)-7-(4-methyl-1-piperazinyl)-1,4-dihydro-4-oxoquinoline-3-carboxylic acid (Reference compound, disclosed in Abstracts of The 1984 ICAAC, page 102)
B. 6-Fluoro-1-(4-fluorophenyl)-7-(1-piperazinyl)-1,4-dihydro-4-oxoquinoline-3-carboxylic acid (Reference compound, disclosed in Abstracts of the 1984 ICAAC, page 102)
C. 6-Fluoro-1-(4-hydroxyphenyl)-7-(4-methyl-1-piperazinyl)-1,4-dihydro-4-oxoquinoline-3-carboxylic acid (Reference compound, disclosed in European Patent Publication No. 0131839)

TABLE 2

| Test microorganisms | Test Compd. No. 1 | | Test Compd. No. 2 | | Test Compd. No. 3 | | Test Compd. No. 4 | |
|---|---|---|---|---|---|---|---|---|
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| Staphylococcus aureus FDA 209P | <0.048 | <0.048 | 0.097 | 0.097 | 0.097 | 0.097 | <0.048 | <0.048 |
| Staphylococcus pyrogens IID S-23 | 0.78 | 0.39 | 3.12 | 0.781 | 0.781 | 0.39 | 0.39 | 0.39 |
| Escherichia coli NIHJ JC-2 | 0.097 | <0.048 | 0.097 | 0.097 | 0.097 | 0.097 | 0.097 | 0.097 |
| Escherichia coli No. 29 | <0.048 | <0.048 | 0.097 | <0.048 | 0.195 | 0.097 | <0.048 | <0.048 |
| Klebsiella pneumoniae NCTC 9632 | <0.097 | 0.097 | 0.097 | 0.097 | <0.048 | 0.097 | 0.097 | 0.097 |
| Proteus inconstans IFO 12930 | 1.56 | 0.78 | 1.56 | 1.56 | 1.56 | 0.781 | 1.56 | 0.781 |
| Proteus morganii IID Kono | 0.39 | 0.195 | 0.39 | 0.39 | 0.781 | 0.781 | 0.781 | 0.39 |
| Serratia marcescens IFO 12648 | 0.39 | 0.195 | 0.39 | 0.39 | 0.781 | 0.781 | 0.781 | 0.781 |
| Acinetobacter calcoaceticus AC-54 | 0.39 | 0.195 | 0.39 | 0.195 | 0.781 | 0.195 | 0.39 | 0.195 |
| Pseudomonas aeruginosa ATCC 10145 | 1.56 | 0.78 | 3.12 | 1.56 | 1.56 | 1.56 | 1.56 | 1.56 |
| Pseudomonas aeruginosa E-2 | 1.56 | 0.78 | 1.56 | 1.56 | 1.56 | 1.56 | 1.56 | 0.781 |
| Bacillus subtilis ATCC 6633 | <0.048 | <0.049 | 0.097 | 0.097 | 0.195 | 0.097 | 0.097 | 0.097 |
| Streptococcus faecalis IFO 12580 | 0.78 | 0.39 | 1.56 | 0.781 | 0.781 | 0.39 | 0.39 | 0.39 |

| Test microorganisms | Test Compd. No. 5 | | Test Compd. A | | Test Compd. B | | Test Compd. C | |
|---|---|---|---|---|---|---|---|---|
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| Staphylococcus aureus FDA 209P | 0.097 | <0.048 | 0.39 | 0.195 | 0.39 | 0.195 | 0.097 | <0.048 |
| Staphylococcus pyrogens IID S-23 | 0.781 | 0.781 | 6.25 | 3.12 | 6.25 | 3.12 | 1.56 | 0.78 |
| Escherichia coli NIHJ JC-2 | 0.097 | 0.097 | 0.195 | 0.195 | 0.097 | <0.048 | 0.097 | 0.097 |
| Escherichia coli No. 29 | 0.097 | <0.048 | 0.195 | 0.097 | 0.097 | <0.048 | 0.097 | <0.048 |
| Klebsiella pneumoniae NCTC 9632 | 0.097 | 0.097 | 0.195 | 0.195 | 0.097 | <0.048 | 0.097 | <0.048 |
| Proteus inconstans IFO 12930 | 1.56 | 0.781 | 3.12 | 3.12 | 0.78 | 0.78 | 0.78 | 0.39 |
| Proteus morganii IID Kono | 0.39 | 0.39 | 0.78 | 0.78 | 0.195 | 0.195 | 0.39 | 0.39 |
| Serratia marcescens IFO 12648 | 0.781 | 0.39 | 3.12 | 0.78 | 0.39 | 0.195 | 0.39 | 0.195 |
| Acinetobacter calcoaceticus AC-54 | 0.39 | 0.195 | 0.39 | 0.39 | 0.39 | 0.195 | 0.39 | 0.195 |
| Pseudomonas aeruginosa ATCC 10145 | 1.56 | 1.56 | 3.12 | 3.12 | 1.56 | 0.78 | 1.56 | 0.78 |
| Pseudomonas aeruginosa E-2 | 1.56 | 0.781 | 3.12 | 3.12 | 0.78 | 0.78 | 0.78 | 0.39 |
| Bacillus subtilis ATCC 6633 | 0.097 | <0.048 | 0.195 | 0.097 | 0.195 | 0.097 | 0.097 | 0.097 |
| Streptococcus faecalis IFO 12580 | 0.781 | 0.39 | — | — | — | — | — | — |

EXPERIMENT 2

(Absorption by oral administration in monkey)

The test compounds were dissolved in 15% aqueous lactic acid (in case of Test Compound 5) or suspended in 0.5% sodium carboxymethyl cellulose solution (in case of Test Compound C). The solution or suspension was administered into stomach of monkey (two monkeyes) with catheter. After the administration of test compounds, the blood was collected from the lower limbs vein at a fixed interval with a syringe treated with heparin. The collected blood was centrifuged at 3,000 r.p.m. for 10 minutes to separate the plasma. The concentration of the test compound was measured by a thin layer cup method (a bio-assay), wherein *Bacillus subtilis* ATCC 6633 was used as a bacteria for determination. Based on a standard curve, the concentration of test compound in plasma was calculated. The results are shown in Table 3.

TABLE 3

| Test comp. No. | Dose (mg/kg) | Run No. | Amount of test compd. in plasma (γ/ml) Time (hour) | | | | | |
|---|---|---|---|---|---|---|---|---|
| | | | 0.5 | 1 | 2 | 4 | 7 | 24 |
| 5 | 90 | 1 | N.D.*1 | 0.632 | 0.752 | 2.340 | N.D.*1 | N.D.*1 |
| | | 2 | N.D.*1 | 0.926 | 1.060 | 1.294 | 1.620 | N.D.*1 |
| | | Average | <0.1 | 0.779 | 0.906 | 1.817 | <0.86 | <0.1 |
| C | 100 | 1 | 0.36 | 0.49 | 0.65 | 0.96 | 0.95 | 0.90 |
| | | 2 | N.D.*2 | N.D.*2 | N.D.*2 | N.D.*2 | N.D.*2 | N.D.*2 |

TABLE 3-continued

| Test comp. No. | Dose (mg/kg) | Run No. | Amount of test compd. in plasma (γ/ml) Time (hour) | | | | | |
|---|---|---|---|---|---|---|---|---|
| | | | 0.5 | 1 | 2 | 4 | 7 | 24 |
| | | Average | <0.28 | <0.35 | <0.43 | <0.58 | <0.58 | <0.55 |

[Note]:
N.D.*1: <0.1 γ/ml.
N.D.*2: <0.2 γ/ml
When the average was counted in case of N.D., it was counted as 0.12 γ/ml or 0.2 γ/ml, respectively, and the average value was shown with a head of "<" (less than)

What is claimed is:

1. 6-Fluoro-1-(4-acetyloxyphenyl)-7-(1,4-diazabicyclo[4.3.0]nonan-1-yl)-1,4-dihydro-4-oxoquinoline-3-carboxylic acid or a pharmaceutically acceptable salt thereof.

2. An antimicrobial composition which comprises as an essential active ingredient an antimicrobially effective amount of 6-fluoro-1-(4-acetyloxyphenyl)-7-(1,4-diazabicyclo[4.3.0]-nonan-1-yl)-1,4-dihydro-4-oxoquinoline-3-carboxylic acid or a pharmaceutically acceptable salt thereof in a conventional pharmaceutically acceptable diluent or carrier.

* * * * *